United States Patent
Altshuler et al.

(10) Patent No.: US 6,562,574 B2
(45) Date of Patent: May 13, 2003

(54) ASSOCIATION OF PROTEIN KINASE C ZETA POLYMORPHISMS WITH DIABETES

(75) Inventors: David M. Altshuler, Brookline, MA (US); Joel N. Hirschhorn, Newton, MA (US); Eric S. Lander, Cambridge, MA (US)

(73) Assignees: Whitehead Institute for Biomedical Research, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 09/842,307

(22) Filed: Apr. 25, 2001

(65) Prior Publication Data

US 2002/0137048 A1 Sep. 26, 2002

Related U.S. Application Data

(60) Provisional application No. 60/199,468, filed on Apr. 25, 2000.

(51) Int. Cl.[7] .......................... C12Q 1/68; C07H 21/02; C07H 21/04; C12P 19/34
(52) U.S. Cl. .......................... 435/6; 435/91.2; 536/23.1; 536/23.5; 536/24.31; 536/24.33
(58) Field of Search .................... 435/6, 91.2; 536/23.1, 536/23.5, 24.31, 24.33

(56) References Cited

U.S. PATENT DOCUMENTS

| | | | |
|---|---|---|---|
| 5,800,992 A | * | 9/1998 | Fodor et al. .................. 435/6 |
| 5,837,832 A | | 11/1998 | Chee et al. .................. 536/22.1 |
| 5,861,242 A | | 1/1999 | Chee et al. .................... 435/5 |
| 6,045,996 A | | 4/2000 | Cronin et al. .................. 435/6 |
| 6,156,601 A | | 12/2000 | McGall et al. ................. 435/6 |

FOREIGN PATENT DOCUMENTS

WO   WO 95/11995   5/1995

OTHER PUBLICATIONS

Watanabe et al. GenBank Accession No. AU027506, Mar. 2, 1999.*
Accession No. AI028426, "Nucleotide Sequence Similar to Human Protein Kinase C Zeta mRNA" (1998).
Kochs, G., et al., "Activation and substrate specificity of the human protein kinase C α and ζ isoenzymes", *European Journal of Biochemistry*, 216(2) : 597–606 (1993).
Haneda M., et al., "Abnormalities in Protein Kinase C and MAP Kinase Cascade in Mesangial Cells Cultured Under High Glucose Conditions", *Journal of Diabetes and Its Complications*, 9: 246–248 (1995).
Saiki, R. K., et al., "Analysis of enzymatically amplified β–globin and HLA–DQα DNA with allele–specific oligonucleotide probes", *Nature*, 324 (13) : 163–166 (1986).
Araki, S. I., et al., "Polymorphisms in Protein Kinase C β (PKCβ) Gene and Risk of Diabetic Nephropathy (DN) in Type 1 Diabetes", *Diabetes*, 49 (1) : 624 (2000).

* cited by examiner

*Primary Examiner*—Carla J. Myers
(74) *Attorney, Agent, or Firm*—Hamilton, Brook, Smith & Reynolds, P.C.

(57) ABSTRACT

A central role for the gene encoding protein kinase C zeta in diabetes and perhaps in related disorders is disclosed. Use of single nucleotide polymorphisms in the protein kinase C zeta gene for diagnosis, prediction of clinical course and treatment response, development of new treatments and development of cell-culture based and animal models for research and treatment are disclosed.

12 Claims, 2 Drawing Sheets

NM_002744. Homo sapiens prote...[gi:4506078]   PubMed, Protein, Related Sequences, LinkOut

```
LOCUS       NM_002744     2146 bp    mRNA           PRI       19-MAR-1999
DEFINITION  Homo sapiens protein kinase C, zeta (PRKCZ) mRNA.
ACCESSION   NM_002744
VERSION     NM_002744.1  GI:4506078
KEYWORDS    .
SOURCE      human.
  ORGANISM  Homo sapiens
            Eukaryota; Metazoa; Chordata; Craniata; Vertebrata; Mammalia;
            Eutheria; Primates; Catarrhini; Hominidae; Homo.
REFERENCE   1  (bases 1 to 2146)
  AUTHORS   Kochs,G., Hummel,R., Meyer,D., Hug,H., Marme,D. and Sarre,T.F.
  TITLE     Activation and substrate specificity of the human protein kinase C
            alpha and zeta isoenzymes
  JOURNAL   Eur. J. Biochem. 216 (2), 597-606 (1993)
  MEDLINE   93387312
REFERENCE   2  (bases 1 to 2146)
  AUTHORS   Hug,H.P.
  TITLE     Direct Submission
  JOURNAL   Submitted (07-SEP-1992) Hubert P. Hug, Deptartment of Molecular
            Biology, Osaka Bioscience, Institute, 6-2-4 Furuedai, Osaka, 565,
            Japan
COMMENT     REFSEQ: This reference sequence was derived from Z15108.
            PROVISIONAL RefSeq: This is a provisional reference sequence record
            that has not yet been subject to human review. The final curated
            reference sequence record may be somewhat different from this one.
FEATURES             Location/Qualifiers
     source          1..2146
                     /organism="Homo sapiens"
                     /db_xref="taxon:9606"
                     /clone="PKC z11"
                     /sex="Female"
                     /tissue_type="Brain-Hippocampus"
                     /clone_lib="LambdaZAPII vector (Stratagene, No.936205)"
                     /dev_stage="2 years old"
     gene            1..2146
                     /gene="PRKCZ"
                     /db_xref="LocusID:5590"
     CDS             7..1761
                     /gene="PRKCZ"
                     /EC_number="2.7.1.-"
                     /codon_start=1
                     /db_xref="LocusID:5590"
                     /product="protein kinase C, zeta"
                     /protein_id="NP_002735.1"
                     /db_xref="GI:4506079"
                     /translation="MEGSGGRVRLKAHYGGDIFITSVDAATTFEELCEEVRDMCRLHQ
                     QHPLTLKWVDSEGDPCTVSSQMELEEEAFRLARQCRDEGLIIHVFPSTPEQPGLPCPGE
                     DKSIYRRGARRWRKLYRANGHLFQAKRFNRRAYCGQCSERIWGLARQGYRCINCKLLV
                     HKRCHGLVPLTCRKHMDSVMPSQEPPVDDKNEDADLPSEETDGIAYISSSRKHDSIKD
                     DSEDLKPVIDGMDGIKISQGLGLQDFDLIRVIGRGSYAKVLLVRLKKNDQIYAMKVVK
                     KELVHDDEDIDWVQTEKHVFEQASSNPFLVGLHSCFQTTSRLFLVIEYVNGGDLMFHM
                     QRQRKLPEEHARFYAAEICIALNFLHERGIIYRDLKLDNVLLDADGHIKLTDYGMCKE
                     GLGPGDTTSTFCGTPNYIAPEILRGEEYGFSVDWWALGVLMFEMMAGRSPFDIITDNP
                     DMNTEDYLFQVILEKPIRIPRFLSVKASHVLKGFLNKDPKERLGCRPQTGFSDIKSHA
                     FFRSIDWDLLEKKQALPPFQPQITDDYGLDNFDTQFTSEPVQLTPDDEDAIKRIDQSE
                     FEGFEYINPLLLSTEESV" (SEQ ID NO: 2)
```

Figure 1A

```
BASE COUNT      506 a    602 c    633 g    405 t
ORIGIN
      1 cccaagatgg aagggagcgg cggccgcgtc cgcctcaagg cgcattacgg gggggacatc
     61 ttcatcacca gcgtggacgc cgccacgacc ttcgaggagc tctgtgagga agtgagagac
    121 atgtgtcgtc tgcaccagca gcacccgctc accctcaagt gggtggacag cgaaggtgac
    181 ccttgcacgg tgtcctccca gatggagctg gaagaggctt tccgcctggc ccgtcagtgc
    241 agggatgaag gcctcatcat tcatgttttc ccgagcaccc ctgagcagcc tggcctgcca
    301 tgtccgggag aagacaaatc tatctaccgc cggggagcca gaagatggag gaagctgtac
    361 cgtgccaacg gccacctctt ccaagccaag cgctttaaca ggagagcgta ctgcggtcag
    421 tgcagcgaga ggatatgggg cctcgcgagg caaggctaca ggtgcatcaa ctgcaaactg
    481 ctggtccata agcgctgcca cggcctcgtc ccgctgacct gcaggaagca tatggattct
    541 gtcatgcctt cccaagagcc tccagtagac gacaagaacg aggacgccga ccttccttcc
    601 gaggagacag atggaattgc ttacatttcc tcatcccgga agcatgacag cattaaagac
    661 gactcggagg accttaagcc agttatcgat gggatggatg gaatcaaaat ctctcagggg
    721 cttgggctgc aggactttga cctaatcaga gtcatcgggc gcgggagcta cgccaaggtt
    781 ctcctggtgc ggttgaagaa gaatgaccaa atttacgcca tgaaagtggt gaagaaagag
    841 ctggtgcatg atgacgagga tattgactgg gtacagacag agaagcacgt gtttgagcag
    901 gcatccagca accccttcct ggtcggatta cactcctgct tccagacgac aagtcggttg
    961 ttcctggtca ttgagtacgt caacggcggg gacctgatgt tccacatgca gaggcagagg
   1021 aagctccctg aggagcacgc caggttctac gcggccgaga tctgcatcgc cctcaacttc
   1081 ctgcacgaga gggggatcat ctacagggac ctgaagctgg acaacgtcct cctggatgcg
   1141 gacgggcaca tcaagctcac agactacggc atgtgcaagg aggcctggg ccctggtgac
   1201 acaacgagca ctttctgcgg aaccccgaat tacatcgccc ccgaaatcct gcggggagag
   1261 gagtacgggt tcagcgtgga ctggtgggcg ctgggagtcc tcatgtttga gatgatggcc
   1321 gggcgctccc cgttcgacat catcaccgac aacccggaca tgaacacaga ggactacctt
   1381 ttccaagtga tcctggagaa gcccatccgg atccccggt tcctgtccgt caaagcctcc
   1441 catgttttaa aaggattttt aaataaggac cccaaagaga ggctcggctg ccggccacag
   1501 actggatttt ctgacatcaa gtcccacgcg ttcttccgca gcatagactg ggacttgctg
   1561 gagaagaagc aggcgctccc tccattccag ccacagatca cagacgacta cggtctggac
   1621 aactttgaca cacagttcac cagcgagccc gtgcagctga ccccagacga tgaggatgcc
   1681 ataaagagga tcgaccagtc agagttcgaa ggctttgagt atatcaaccc attattgctg
   1741 tccaccgagg agtcggtgtg aggccgcgtg cgtctctgtc gtggacacgc gtgattgacc
   1801 ctttaactgt atccttaacc accgcatatg catgccaggc tgggcacggc tccgagggcg
   1861 gccagggaca gacgcttgcg ccgagaccgc agagggaagc gtcagcgggc gctgctggga
   1921 gcagaacagt ccctcacacc tggcccggca ggcagcttcg tgctggagga acttgctgct
   1981 gtgcctgcgt cgcggcggat ccgcgggac cctgccgagg gggctgtcat gcggtttcca
   2041 aggtgcacat tttccacgga aacagaactc gatgcactga cctgctccgc caggaaagtg
   2101 agcgtgtagc gtcctgagga ataaaatgtt ccgatgaaaa aaaaaa (SEQ ID NO: 1)
```

Figure 1B

ASSOCIATION OF PROTEIN KINASE C ZETA POLYMORPHISMS WITH DIABETES

RELATED APPLICATION

This application claims the benefit of U.S. Provisional Application No. 60/199,468, filed on Apr. 25, 2000, the entire teachings of which are incorporated herein by reference.

BACKGROUND OF THE INVENTION

Diabetes, one of the most insidious of the major diseases, can strike suddenly or lie undiagnosed for years while attacking the blood vessels and nerves. Diabetics, as a group, are far more often afflicted with blindness, heart disease, stroke, kidney disease, hearing loss, gangrene and impotence than non-diabetics, and diabetes and its complications are a leading cause of death in this country.

Diabetes adversely affects the way the body uses sugars and starches which, during digestion, are converted into glucose. Insulin, a hormone produced by the pancreas, makes the glucose available to the body's cells for energy. The net effect of insulin is to promote the storage and use of carbohydrates, protein and fat. Insulin deficiency is a common and serious pathologic condition in humans. In Type I diabetes the pancreas produces little or no insulin, and insulin must be injected daily for the survival of the diabetic. In Type II diabetes the pancreas produces insulin, but the amount of insulin is insufficient and/or less than fully effective due to cellular resistance. In either form there are widespread abnormalities, but the fundamental defects to which the abnormalities can be traced are (1) a reduced entry of glucose into various "peripheral" tissues and (2) an increased liberation of glucose into the circulation from the liver (increased hepatic glucogenesis). There is therefore an extracellular glucose excess and an intracellular glucose deficiency. There is also a decrease in the entry of amino acids into muscle and an increase in lipolysis. These defects result in elevated levels of glucose in the blood, and prolonged high blood sugar.

Obesity and insulin resistance, the latter of which is generally accompanied by hyperinsulinemia or hyperglycemia, or both, are hallmarks of Type II diabetes. Despite decades of research related to these serious health problems, the etiology of type II diabetes is unknown.

SUMMARY OF THE INVENTION

As part of an ongoing study to identify genes which contribute to the risk of type II diabetes, association tests with polymorphisms within genes of biological interest were performed. One such gene, the gene encoding protein kinase C zeta (see FIGS. 1A–1B), was found to contain two common polymorphisms within its coding region. Work described herein has demonstrated an association of at least one of these polymorphisms with type II diabetes. Specifically, this work has identified an approximately 60% decrease in risk associated with the rare version (a C at position 246 (which is a T in the more common version)) of this polymorphism (significant to a p value of 0.002). Such an association has not previously been described.

Furthermore, the data suggest that the actual mutation influencing disease is not one of the two identified polymorphisms but rather that these polymorphisms may be reflecting the nearby action of another mutation which is in linkage disequilibrium with the SNP(s).

These results demonstrate a central role for the gene encoding PKC zeta in diabetes, and perhaps in related disorders. Study of the altered function of the mutant gene may guide drug discovery efforts. Moreover, a diagnostic test can be developed based on one or both of the mutations and/or the as-yet unidentified mutation to guide patient treatment. Thus, the invention relates to the SNPs identified as described herein, as well as to the use of these SNPs and others nearby in linkage disequilibrium with the identified SNPs for diagnosis, prediction of clinical course and treatment response, development of new treatments based upon comparison of the variant and normal versions of the gene or gene product, and development of cell-culture based and animal models for research and treatment. The invention further relates to novel compounds and pharmaceutical compositions for use in the diagnosis and treatment of such disorders.

The invention further relates to a method of diagnosing or aiding in the diagnosis of a disorder associated with the presence of a thymine at nucleotide position 246 of SEQ ID NO: 1 (e.g., diabetes) in an individual comprising obtaining a nucleic acid sample from the individual and determining the nucleotide present at nucleotide position 246 of SEQ ID NO: 1, wherein presence of a thymine at said position is indicative of increased likelihood of diabetes in the individual as compared with an appropriate control, e.g., an individual having a cytosine at said position. The invention further relates to a method of diagnosing or aiding in the diagnosis of a disorder associated with the presence of a thymine at nucleotide position 246 of SEQ ID NO: 1 (e.g., diabetes) in an individual comprising obtaining a nucleic acid sample from the individual and determining the nucleotide present at nucleotide position 246 of SEQ ID NO: 1, wherein presence of a cytosine at said position is indicative of decreased likelihood of diabetes in the individual as compared with an appropriate control, e.g., an individual having a thymine at said position.

In one embodiment, the invention relates to a method for predicting the likelihood that an individual will have diabetes (or aiding in the diagnosis of diabetes), comprising the steps of obtaining a DNA sample from an individual to be assessed and determining the nucleotide present at nucleotide position 246 of the PKC zeta gene. The presence of a "C" (the variant nucleotide) at position 246 indicates that the individual has a lower likelihood of having diabetes than an individual having a "T" at that position, or a lower likelihood of having severe symptomology. In a particular embodiment, the individual is an individual at risk for development of diabetes.

In another embodiment, the invention relates to pharmaceutical compositions comprising a variant PKC zeta gene product for use in the treatment of diabetes and related disorders. The invention further relates to the use of compositions (i.e., agonists and antagonists) which enhance or increase or which reduce or decrease, respectively, the activity of a variant PKC zeta gene product for use in the treatment of diabetes. The invention also relates to the use of a nucleic acid molecule encoding a variant PKC zeta gene product for use in the treatment of diabetes.

BRIEF DESCRIPTION OF THE DRAWINGS

FIGS. 1A–B show the reference nucleotide (SEQ ID NO: 1) and amino acid (SEQ ID NO: 2) sequences for the PKC zeta gene and gene product.

DETAILED DESCRIPTION OF THE INVENTION

Work described herein has demonstrated an association of at least one polymorphism in the PKC zeta gene with type II diabetes. Specifically, this work has identified an approximately 60% decrease in risk associated with the rare version (nucleotide C at position 246 (which is nucleotide T in the more common version)) of this polymorphism (significant to a p value of 0.002). The polymorphism and flanking sequence are: CCGTCAGTGCAGGGA[T/C]GAAGGCCTCATCATT which consists of nucleotides 231 to 261 of SEQ ID NO: 1. Such an association has not previously been described.

Furthermore, the data suggest that the actual mutation influencing disease is not one of the two identified polymorphisms but rather that these polymorphisms may be reflecting the nearby action of another mutation. First, the associated polymorphisms identified herein are silent mutations that do not change the encoded protein. Furthermore, when the two mutations are combined, there is an apparently greater effect than with either alone. This implies linkage disequilibrium with an as-yet undiscovered mutation in the nearby vicinity.

These results demonstrate a central role for the gene encoding PKC zeta in diabetes, and perhaps in related disorders. Study of the altered function of the mutant gene may guide drug discovery efforts. Moreover, a diagnostic test can be developed based on one or both of the mutations or the as-yet unidentified mutation to guide patient treatment. Thus, the invention relates to the SNP identified as described herein, as well as to the use of this SNP and others nearby in linkage disequilibrium with the SNP for diagnosis, prediction of clinical course and treatment response, development of new treatments based upon comparison of the variant and normal versions of the gene or gene product, and development of cell-culture based and animal models for research and treatment. Relevant disorders include, but are not limited to, diabetes, obesity, polycystic ovarian syndrome, cholesterol disorders, diabetic complications (for example, kidney failure, blindness, nerve damage, heart attack), stroke, hearing loss, gangrene and hypertension. It is understood that although the invention is exemplified using diabetes, the invention is also applicable to these and other related disorders. The invention further relates to novel compounds and pharmaceutical compositions for use in the diagnosis and treatment of such disorders.

As used herein, polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair, in which case it is referred to as a single nucleotide polymorphism.

As described herein, it has been discovered that a polymorphism in the gene for PKC zeta is negatively correlated with incidence of diabetes. In particular, it has been discovered that one or more single nucleotide polymorphisms within the nucleotide sequence encoding the PKC zeta gene product are correlated with a reduced incidence of diabetes in the sample population assessed as described herein. In one embodiment, a single polymorphism from T to C at nucleotide position 246 in FIGS. 1A–B, or at a nucleotide position corresponding thereto, is correlated with a reduced incidence of diabetes in the sample population assessed as described herein.

Data from the work described herein has shown that there is a variation from random (i.e., that which would be expected by chance) in the transmission of the reference (T) and variant (C) alleles from a parent who is heterozygous for the PKC zeta alleles to an offspring diagnosed with diabetes. The variant allele (C) is transmitted less frequently to the diabetic offspring than would be expected by chance, while the reference allele (T) is transmitted more frequently than would be expected by chance. Thus, it appears that the variant allele may contribute to protection or reduction in symptomology with respect to diabetes. Alternatively, this particular polymorphism may be one of a group of two or more polymorphisms in the PKC zeta gene which contributes to the presence, absence, or severity of diabetes and related disorders.

Thus, the invention relates to a method for predicting the likelihood that an individual will have diabetes, or for aiding in the diagnosis of diabetes, or predicting the likelihood of having reduced symptomology associated with diabetes, comprising the steps of obtaining a DNA sample from an individual to be assessed and determining the nucleotide present at nucleotide position 246 of the PKC zeta gene. The presence of a "C" (the variant nucleotide) at position 246 indicates that the individual has a lower likelihood of having diabetes, or a lower likelihood of having severe symptomology associated with diabetes, than if that individual had the reference nucleotide at that position. Conversely, the presence of a "T" (the reference nucleotide) at position 246 indicates that the individual has a greater likelihood of having diabetes, or a likelihood of having increased symptomology associated with diabetes, than if that individual had the variant nucleotide at that position. In a particular embodiment, the individual is an individual at risk for development of diabetes. In another embodiment the individual exhibits clinical symptomology associated with diabetes. In one embodiment, the individual has been clinically diagnosed as having diabetes.

The genetic material to be assessed can be obtained from any nucleated cell from the individual. For assay of genomic DNA, virtually any biological sample (other than pure red blood cells) is suitable. For example, convenient tissue samples include whole blood, semen, saliva, tears, urine, fecal material, sweat, skin and hair. For assay of cDNA or mRNA, the tissue sample must be obtained from an organ in which the target nucleic acid is expressed. For example, cells from the central nervous system (such as cells of the hippocampus) are suitable sources for obtaining cDNA for the PKC zeta gene.

Many of the methods described herein require amplification of DNA from target samples. This can be accomplished by e.g., PCR. *See generally PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The nucleotide which occupies the polymorphic site of interest (e.g., nucleotide position 246 in PKC zeta) can be identified by a variety methods, such as Southern analysis of genomic DNA; direct mutation analysis by restriction enzyme digestion; Northern analysis of RNA; denaturing high pressure liquid chromatography (DHPLC); gene isolation and sequencing; hybridization of an allele-specific oligonucleotide with amplified gene products; single base extension (SBE). In a preferred embodiment, determination of the allelic form of PKC zeta is carried out using SBE-FRET methods as described herein, or using chip-based oligonucleotide arrays as described herein. A sampling of suitable procedures are discussed below in turn.

1. Allele-Specific Probes

The design and use of allele-specific probes for analyzing polymorphisms is described by e.g., Saiki et al., *Nature* 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some examples of which are described in WO 95/11995. WO 95/11995 also describes subarrays that are optimized for detection of a variant form of a precharacterized polymorphism. Such a subarray contains probes designed to be complementary to a second reference sequence, which is an allelic variant of the first reference sequence. The second group of probes is designed by the same principles, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarity. See Gibbs, *Nucleic Acid Res.* 17, 2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

4. Direct-Sequencing

The direct analysis of the sequence of polymorphisms of the present invention can be accomplished using either the dideoxy chain termination method or the Maxam-Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., *PCR Technology, Principles and Applications for DNA Amplification*, (W. H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., *Proc. Nat. Acad. Sci.* 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

7. Single-Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al., (*PNAS* 94:10756-61 (1997), incorporated herein by reference) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

The polymorphism of the invention may contribute to the protection of an individual against diabetes in different ways. The polymorphism may exert phenotypic effects indirectly via influence on replication, transcription, and translation. Additionally, the described polymorphism may predispose an individual to a distinct mutation that is causally related to a certain phenotype, such as susceptibility or resistance to diabetes and related disorders. The discovery of the polymorphism and its correlation with diabetes facilitates biochemical analysis of the variant and the development of assays to characterize the variant and to screen for pharmaceutical agents that interact directly with one or another form of the protein.

Alternatively, this particular polymorphism may be one of a group of two or more polymorphisms in the PKC zeta gene which contributes to the presence, absence or severity of diabetes. An assessment of other polymorphisms within the PKC zeta gene can be undertaken, and the separate and combined effects of these polymorphisms on the neuropsychiatric disorder phenotype can be assessed.

Correlation between a particular phenotype, e.g., the diabetic phenotype, and the presence or absence of a particular allele is performed for a population of individuals who have been tested for the presence or absence of the phenotype. Correlation can be performed by standard statistical methods such as a Chi-squared test and statistically significant correlations between polymorphic form(s) and phenotypic characteristics are noted. For example, as described herein, it has been found that the presence of the PKC zeta variant allele, having a C at polymorphic site 246, correlates negatively with diabetes with a p value of p=0.002 by Chi-squared test.

This correlation can be exploited in several ways. In the case of a strong correlation between a particular polymorphic form, e.g., the reference allele for PKC zeta and a disease for which treatment is available, e.g., diabetes, detection of the polymorphic form in an individual may justify immediate administration of treatment, or at least the institution of regular monitoring of the individual. Detection of a polymorphic form correlated with a disorder in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic form and a particular disorder, immediate therapeutic intervention or monitoring may not be justified. Nevertheless, the individual can be motivated to begin simple life-style changes (e.g., diet modification, therapy or counseling) that can be accomplished at little cost to the individual but confer potential benefits in reducing the risk of conditions to which the individual may have increased susceptibility by virtue of the particular allele. Furthermore, identification of a polymorphic form correlated with enhanced receptiveness to one of several treatment regimes for a disorder indicates that this treatment regimen should be followed for the individual in question.

Furthermore, it may be possible to identify a physical linkage between a genetic locus associated with a trait of interest (e.g., diabetes) and polymorphic markers that are or are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., *Proc. Natl. Acad. Sci.* (USA) 83, 7353–7357 (1986); Lander et al., *Proc. Natl. Acad. Sci.* (USA) 84, 2363–2367 (1987); Donis-Keller et al., *Cell* 51, 319–337 (1987); Lander et al., *Genetics* 121, 185–199 (1989)). Genes localized by linkage can be cloned by a process known as directional cloning. See Wainwright, *Med. J. Australia* 159, 170–174 (1993); Collins, *Nature Genetics* 1, 3–6 (1992).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., *Science* 245, 1073–1080 (1989); Monaco et al., *Nature* 316, 842 (1985); Yamoka et al., *Neurology* 40, 222–226 (1990); Rossiter et al., *FASEB Journal* 5, 21–27 (1991).

Linkage is analyzed by calculation of LOD (log of the odds) values. A lod value is the relative likelihood of obtaining observed segregation data for a marker and a genetic locus when the two are located at a recombination fraction $\theta$, versus the situation in which the two are not linked, and thus segregating independently (Thompson & Thompson, *Genetics in Medicine* (5th ed, W. B. Saunders Company, Philadelphia, 1991); Strachan, "Mapping the human genome" in *The Human Genome* (BIOS Scientific Publishers Ltd, Oxford), Chapter 4). A series of likelihood ratios are calculated at various recombination fractions ($\theta$), ranging from $\theta=0.0$ (coincident loci) to $\theta=0.50$ (unlinked). Thus, the likelihood at a given value of $\theta$ is: probability of data if loci linked at $\theta$ to probability of data if loci unlinked. The computed likelihoods are usually expressed as the $\log_{10}$ of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of $\theta$ (e.g., LIPED, MLINK (Lathrop, *Proc. Nat. Acad. Sci.* (USA) 81, 3443–3446 (1984)). For any particular lod score, a recombination fraction may be determined from mathematical tables. See Smith et al., *Mathematical tables for research workers in human genetics* (Churchill, London, 1961); Smith, *Ann. Hum. Genet.* 32, 127–150 (1968). The value of $\theta$ at which the lod score is the highest is considered to be the best estimate of the recombination fraction.

Positive lod score values suggest that the two loci are linked, whereas negative values suggest that linkage is less likely (at that value of $\theta$) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of −2 or less is taken as definitive evidence against linkage of the two loci being compared. Negative linkage data are useful in excluding a chromosome or a segment thereof from consideration. The search focuses on the remaining non-excluded chromosomal locations.

In another embodiment, the invention relates to pharmaceutical compositions comprising a variant PKC zeta gene product for use in the treatment of diabetes. As used herein, a variant PKC zeta gene product is intended to mean gene products which are encoded by the variant allele of the PKC zeta gene. The invention further relates to the use of compositions (i.e., agonists) which enhance or increase the activity of the variant PKC zeta gene product, or a functional portion thereof, for use in the treatment of diabetes. The invention also relates to the use of compositions (i.e., antagonists) which reduce or decrease the activity of the variant PKC zeta gene product, or a functional portion thereof, for use in the treatment of diabetes.

In addition to substantially full-length polypeptides expressed by variant genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

For instance, the variant polypeptide or protein, or fragment thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous peptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents and treatment regimens.

Polyclonal and/or monoclonal antibodies that specifically bind to variant gene products but not to corresponding reference gene products are also provided. Antibodies can be made by injecting mice or other animals with the variant gene product or synthetic peptide fragments thereof comprising the variant portion. Monoclonal antibodies are screened as are described, for example, in Harlow & Lane, *Antibodies, A Laboratory Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

The invention further pertains to compositions, e.g., vectors, comprising a nucleotide sequence encoding variant PKC zeta gene product. For example, variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like.

It is also contemplated that cells can be engineered to express the variant allele of the invention by gene therapy methods. For example, DNA encoding the variant PKC zeta gene product, or an active fragment or derivative thereof, can be introduced into an expression vector, such as a viral vector, and the vector can be introduced into appropriate cells in an animal. In such a method, the cell population can be engineered to inducibly or constitutively express active variant PKC zeta gene product. In a preferred embodiment, the vector is delivered to the bone marrow, for example as described in Corey et al. (*Science* 244:1275–1281 (1989)).

The invention also relates to constructs which comprise a vector into which a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc.

The expression vectors of the invention can be introduced into host cells to thereby produce proteins or peptides, including fusion proteins or peptides, encoded by nucleic acids as described herein. The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a nucleic acid of the invention can be expressed in bacterial cells (e.g., *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid of the invention have been introduced. Such host cells can then be used to create non-human transgenic animals in which exogenous nucleotide sequences have been introduced into their genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid of the invention into the male pronuclei of a fertilized oocyte, e.g., by microinjection, retroviral infection, and allowing the oocyte to develop in a pseudopregnant female foster animal. The sequence can be introduced as a transgene into the genome of a non-human animal. Intronic sequences and polyadenylation signals can also be included in the transgene to increase the efficiency of expression of the transgene. A tissue-specific regulatory sequence(s) can be operably linked to the transgene to direct expression of a polypeptide in particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA in tissues or cells of the animals. A transgenic founder animal can then be used to breed additional animals carrying the transgene. Moreover, transgenic animals carrying a transgene encoding the transgene can further be bred to other transgenic animals carrying other transgenes.

The invention also relates to the use of the variant and wildtype gene products to guide efforts to identify the causative mutation for diabetes or to identify or synthesize agents useful in the treatment of diabetes. Amino acids that are essential for function can be identified by methods known in the art, such as site-directed mutagenesis or alanine-scanning mutagenesis (Cunningham et al., *Science*, 244:1081–1085 (1989)). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al., *J. Mol. Biol.*, 224:899–904 (1992); de Vos et al. *Science*, 255:306–312 (1992)).

The present invention also pertains to diagnostic assays and prognostic assays used for prognostic (predictive) purposes to thereby treat an individual prophylactically. Accordingly, one aspect of the present invention relates to diagnostic assays for determining protein and/or nucleic acid expression as well as activity of proteins of the invention, in the context of a biological sample (e.g., blood, serum, cells, tissue) to thereby determine whether an individual is afflicted with a disease or disorder, or is at risk of developing a disorder, e.g., diabetes, associated with aberrant expression or activity. The invention also provides for prognostic (or predictive) assays for determining whether an individual is at risk of developing a disorder associated with activity or expression of proteins or nucleic acids of the invention.

Another aspect of the invention pertains to monitoring the influence of agents (e.g., drugs, compounds) on the expression or activity of proteins of the invention in clinical trials. An exemplary method for detecting the presence or absence of proteins or nucleic acids of the invention in a biological sample involves obtaining a biological sample from a test subject and contacting the biological sample with a compound or an agent capable of detecting the protein, or nucleic acid (e.g., mRNA, genomic DNA) that encodes the protein, such that the presence of the protein or nucleic acid is detected in the biological sample. A preferred agent for detecting mRNA or genomic DNA is a labeled nucleic acid probe capable of hybridizing to mRNA or genomic DNA sequences described herein, preferably in an allele-specific manner. The nucleic acid probe can be, for example, a full-length nucleic acid, or a portion thereof, such as an oligonucleotide of at least 15, 30, 50, 100, 250 or 500 nucleotides in length and sufficient to specifically hybridize under stringent conditions to appropriate mRNA or genomic DNA. Other suitable probes for use in the diagnostic assays of the invention are described herein.

The term "biological sample" is intended to include tissues, calls and biological fluids isolated from a subject, as well as tissues, cells and fluids present within a subject. For example, the sample can be obtained from a tissue selected from the group consisting of: brain tissue, CNS, lung, fetal lung, testis, lymphocytes, adipose, fibroblasts, skeletal muscle, pancreas, uterus, kidney, tonsil, embryo and isolated cells thereof. That is, the detection method of the invention can be used to detect mRNA, protein, or genomic DNA of the invention in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of protein include introducing into a subject a labeled anti-protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample or biopsy sample isolated by conventional means from a subject. A nucleic acid sample is a sample, e.g., a biological sample, which contains nucleic acid molecules.

The invention also encompasses kits for detecting the presence of proteins or nucleic acid molecules of the invention in a biological sample. For example, the kit can comprise a labeled compound or agent capable of detecting protein or mRNA in a biological sample; means for determining the amount of in the sample; and means for comparing the amount of in the sample with a standard. The compound or agent can be packaged in a suitable container. The kit can further comprise instructions for using the kit to detect protein or nucleic acid.

EXAMPLES

In a population of 333 parent-offspring trios, where the offspring had impaired glucose homeostasis (type 2 diabetes, impaired fasting glucose or impaired glucose tolerance), the more common allele was transmitted 130 out of 228 times from heterozygous parents, for a transmission ratio of 0.75 (vs. expected of 1), p<0.05. A similar effect was seen in an independent case-control population of diabetics, with the more common allele over-represented in affected individuals, p<0.01.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of diagnosing or aiding in the diagnosis of diabetes in an individual comprising
   a) obtaining a nucleic acid sample from the individual; and
   b) determining the nucleotide present at nucleotide position 246 of the protein kinase C zeta gene, wherein presence of a thymine at said position is indicative of increased likelihood of diabetes in the individual as compared with an individual having a cytosine at said position.

2. The method of claim 1, wherein the protein kinase C zeta gene has the nucleotide sequence of SEQ ID NO: 1.

3. The method of claim 1, wherein the nucleic acid sample is obtained from a tissue selected from the group consisting of brain tissue and CNS and isolated cells thereof.

4. The method of claim 3, wherein the brain tissue is obtained from the hippocampus.

5. A method of diagnosing or aiding in the diagnosis of diabetes in an individual comprising
   a) obtaining a nucleic acid sample from the individual; and
   b) determining the nucleotide present at nucleotide position 246 of the protein kinase C zeta gene, wherein presence of a cytosine at said position is indicative of decreased likelihood of diabetes in the individual as compared with an individual having a thymine at said position.

6. The method according to claim 5, wherein the protein kinase C zeta gene has the nucleotide sequence of SEQ ID NO: 1.

7. A method for predicting the likelihood that an individual will have diabetes, comprising the steps of:
   a) obtaining a DNA sample from an individual to be assessed; and
   b) determining the nucleotide present at nucleotide position 246 of the protein kinase C zeta gene, wherein the presence of a "C" at position 246 indicates that the individual has a lower likelihood of having diabetes than an individual having a "T" at that position.

8. The method according to claim 7, wherein the protein kinase C zeta gene has the nucleotide sequence of SEQ ID NO: 1.

9. A method according to claim 7, wherein the individual is an individual at risk for development of diabetes.

10. A method for predicting the likelihood that an individual will have reduced symptomology associated with diabetes, comprising the steps of:
    a) obtaining a DNA sample from an individual to be assessed; and
    b) determining the nucleotide present at nucleotide position 246 of the protein kinase C zeta gene, wherein the presence of a "C" at position 246 indicates that the individual has a greater likelihood of having reduced symptomology associated with diabetes than an individual having a "T" at that position.

11. The method according to claim 9, wherein the protein Kinase C zeta gene has the nucleotide sequence of SEQ ID NO: 1.

12. An isolated nucleic acid molecule comprising the nucleic acid sequence of SEQ ID NO: 1 with the exception that the nucleic acid sequence comprises a cytosine at nucleotide position 246 of SEQ ID NO: 1.

* * * * *

SEQUENCE LISTING

```
<160> NUMBER OF SEQ ID NOS: 2

<210> SEQ ID NO 1
<211> LENGTH: 2146
<212> TYPE: DNA
<213> ORGANISM: Homo sapiens

<400> SEQUENCE: 1
cccaagatgg aagggagcgg cggccgcgtc cgcctcaagg cgcattacgg gggggacatc      60
ttcatcacca gcgtggacgc cgccacgacc ttcgaggagc tctgtgagga agtgagagac     120
atgtgtcgtc tgcaccagca gcacccgctc accctcaagt gggtggacag cgaaggtgac     180
ccttgcacgg tgtcctccca gatggagctg gaagaggctt tccgcctggc ccgtcagtgc     240
```

-continued

```
agggatgaag gcctcatcat tcatgttttc ccgagcaccc ctgagcagcc tggcctgcca     300
tgtccgggag aagacaaatc tatctaccgc cggggagcca agatggag gaagctgtac      360
cgtgccaacg gccacctctt ccaagccaag cgctttaaca ggagagcgta ctgcggtcag    420
tgcagcgaga ggatatgggg cctcgcgagg caaggctaca ggtgcatcaa ctgcaaactg    480
ctggtccata gcgctgcca cggcctcgtc ccgctgacct gcaggaagca tatggattct    540
gtcatgcctt cccaagagcc tccagtagac gacaagaacg aggacgccga ccttccttcc    600
gaggagacac atggaattgc ttacatttcc tcatcccgga agcatgacag cattaaagac    660
gactcggagg accttaagcc agttatcgat gggatggatg aatcaaaat ctctcagggg    720
cttgggctgc aggactttga cctaatcaga gtcatcgggc gcgggagcta cgccaaggtt    780
ctcctggtgc ggttgaagaa gaatgaccaa atttacgcca tgaaagtggt gaagaaagag    840
ctggtgcatg atgacgagga tattgactgg gtacagacag agaagcacgt gtttgagcag    900
gcatccagca cccccttcct ggtcggatta cactcctgct ccagacgac aagtcggttg    960
ttcctggtca ttgagtacgt caacggcggg gacctgatgt ccacatgca gaggcagagg   1020
aagctccctg aggagcacgc caggttctac gcggccgaga tctgcatcgc cctcaacttc   1080
ctgcacgaga gggggatcat ctacaggac ctgaagctgg acaacgtcct cctggatgcg   1140
gacgggcaca tcaagctcac agactacggc atgtgcaagg aaggcctggg ccctggtgac   1200
acaacgagca ctttctgcgg aaccccgaat tacatcgccc ccgaaatcct gcggggagag   1260
gagtacgggt tcagcgtgga ctggtgggcg ctggagtcc tcatgtttga gatgatggcc   1320
gggcgctccc cgttcgacat catcaccgac aacccggaca tgaacacaga ggactacctt   1380
ttccaagtga tcctggagaa gcccatccgg atcccccggt tcctgtccgt caaagcctcc   1440
catgttttaa aaggattttt aaataaggac cccaagagaa ggctcggctg ccggccacag   1500
actggatttt ctgacatcaa gtcccacgcg ttcttccgca gcatagactg ggacttgctg   1560
gagaagaagc aggcgctccc tccattccag ccacagatca cagacgacta cggtctggac   1620
aactttgaca cacagttcac cagcgagccc gtgcagctga ccccagacga tgaggatgcc   1680
ataaagagga tcgaccagtc agagttcgaa ggctttgagt atatcaaccc attattgctg   1740
tccaccgagt agtcggtgtg aggccgcgtg cgtctctgtc gtggacacgc gtgattgacc   1800
ctttaactgt atccttaacc accgcatatg catgccaggc tgggcacggc tccgagggcg   1860
gccagggaca gacgcttgcg ccgagaccgc agagggaagc gtcagcgggc gctgctggga   1920
gcagaacagt ccctcacacc tggcccggca ggcagcttcg tgctggagga acttgctgct   1980
gtgcctgcgt cgcggcggat ccgcggggac cctgccgagg gggctgtcat gcggtttcca   2040
aggtgcacat tttccacgga aacagaactc gatgcactga cctgctccgc caggaaagtg   2100
agcgtgtagc gtcctgagga ataaaatgtt ccgatgaaaa aaaaaa                  2146
```

<210> SEQ ID NO 2
<211> LENGTH: 584
<212> TYPE: PRT
<213> ORGANISM: Homo sapiens

<400> SEQUENCE: 2

```
Met Glu Gly Ser Gly Gly Arg Val Arg Leu Lys Ala His Tyr Gly Gly
 1               5                  10                  15

Asp Ile Phe Ile Thr Ser Val Asp Ala Ala Thr Thr Phe Glu Glu Leu
            20                  25                  30

Cys Glu Glu Val Arg Asp Met Cys Arg Leu His Gln Gln His Pro Leu
```

```
                  35                  40                  45
Thr Leu Lys Trp Val Asp Ser Glu Gly Asp Pro Cys Thr Val Ser Ser
    50                  55                  60
Gln Met Glu Leu Glu Ala Phe Arg Leu Ala Arg Gln Cys Arg Asp
 65                  70                  75                  80
Glu Gly Leu Ile Ile His Val Phe Pro Ser Thr Pro Glu Gln Pro Gly
                     85                  90                  95
Leu Pro Cys Pro Gly Glu Asp Lys Ser Ile Tyr Arg Arg Gly Ala Arg
                100                 105                 110
Arg Trp Arg Lys Leu Tyr Arg Ala Asn Gly His Leu Phe Gln Ala Lys
            115                 120                 125
Arg Phe Asn Arg Arg Ala Tyr Cys Gly Gln Cys Ser Glu Arg Ile Trp
        130                 135                 140
Gly Leu Ala Arg Gln Gly Tyr Arg Cys Ile Asn Cys Lys Leu Leu Val
145                 150                 155                 160
His Lys Arg Cys His Gly Leu Val Pro Leu Thr Cys Arg Lys His Met
                165                 170                 175
Asp Ser Val Met Pro Ser Gln Glu Pro Pro Val Asp Asp Lys Asn Glu
                180                 185                 190
Asp Ala Asp Leu Pro Ser Glu Glu Thr Asp Gly Ile Ala Tyr Ile Ser
            195                 200                 205
Ser Ser Arg Lys His Asp Ser Ile Lys Asp Asp Ser Glu Asp Leu Lys
        210                 215                 220
Pro Val Ile Asp Gly Met Asp Gly Ile Lys Ile Ser Gln Gly Leu Gly
225                 230                 235                 240
Leu Gln Asp Phe Asp Leu Ile Arg Val Ile Gly Arg Gly Ser Tyr Ala
                245                 250                 255
Lys Val Leu Leu Val Arg Leu Lys Lys Asn Asp Gln Ile Tyr Ala Met
                260                 265                 270
Lys Val Val Lys Lys Glu Leu Val His Asp Asp Glu Asp Ile Asp Trp
            275                 280                 285
Val Gln Thr Glu Lys His Val Phe Glu Gln Ala Ser Ser Asn Pro Phe
        290                 295                 300
Leu Val Gly Leu His Ser Cys Phe Gln Thr Thr Ser Arg Leu Phe Leu
305                 310                 315                 320
Val Ile Glu Tyr Val Asn Gly Gly Asp Leu Met Phe His Met Gln Arg
                325                 330                 335
Gln Arg Lys Leu Pro Glu Glu His Ala Arg Phe Tyr Ala Ala Glu Ile
                340                 345                 350
Cys Ile Ala Leu Asn Phe Leu His Glu Arg Gly Ile Ile Tyr Arg Asp
            355                 360                 365
Leu Lys Leu Asp Asn Val Leu Leu Asp Ala Asp Gly His Ile Lys Leu
        370                 375                 380
Thr Asp Tyr Gly Met Cys Lys Glu Gly Leu Gly Pro Gly Asp Thr Thr
385                 390                 395                 400
Ser Thr Phe Cys Gly Thr Pro Asn Tyr Ile Ala Pro Glu Ile Leu Arg
                405                 410                 415
Gly Glu Glu Tyr Gly Phe Ser Val Asp Trp Trp Ala Leu Gly Val Leu
                420                 425                 430
Met Phe Glu Met Met Ala Gly Arg Ser Pro Phe Asp Ile Ile Thr Asp
            435                 440                 445
Asn Pro Asp Met Asn Thr Glu Asp Tyr Leu Phe Gln Val Ile Leu Glu
        450                 455                 460
```

-continued

```
Lys Pro Ile Arg Ile Pro Arg Phe Leu Ser Val Lys Ala Ser His Val
465                 470                 475                 480

Leu Lys Gly Phe Leu Asn Lys Asp Pro Lys Glu Arg Leu Gly Cys Arg
                485                 490                 495

Pro Gln Thr Gly Phe Ser Asp Ile Lys Ser His Ala Phe Phe Arg Ser
                500                 505                 510

Ile Asp Trp Asp Leu Leu Glu Lys Lys Gln Ala Leu Pro Pro Phe Gln
            515                 520                 525

Pro Gln Ile Thr Asp Asp Tyr Gly Leu Asp Asn Phe Asp Thr Gln Phe
        530                 535                 540

Thr Ser Glu Pro Val Gln Leu Thr Pro Asp Asp Glu Asp Ala Ile Lys
545                 550                 555                 560

Arg Ile Asp Gln Ser Glu Phe Glu Gly Phe Glu Tyr Ile Asn Pro Leu
                565                 570                 575

Leu Leu Ser Thr Glu Glu Ser Val
            580
```